(12) United States Patent
Joks et al.

(10) Patent No.: US 7,407,764 B2
(45) Date of Patent: Aug. 5, 2008

(54) PLASMA C5A LEVELS AS AN INDICATOR OF ASTHMA SEVERITY

(75) Inventors: Rauno Joks, Port Washington, NY (US); Hazel P. Drew, Laurelton, NY (US); Myrelle B. Castro, Wallkill, NY (US); Nandita Mathur Khaneja, Kew Gardens Hills, NY (US)

(73) Assignee: The Research Foundation of State University of New York, Albany, NY (US)

( * ) Notice: Subject to any disclaimer, the term of this patent is extended or adjusted under 35 U.S.C. 154(b) by 0 days.

(21) Appl. No.: 11/251,658

(22) Filed: Oct. 17, 2005

(65) Prior Publication Data

US 2006/0110780 A1    May 25, 2006

Related U.S. Application Data

(63) Continuation-in-part of application No. PCT/US2004/011348, filed on Apr. 13, 2004.

(60) Provisional application No. 60/463,646, filed on Apr. 17, 2003.

(51) Int. Cl.
*G01N 33/53* (2006.01)

(52) U.S. Cl. .................. 435/7.1; 435/7.2; 435/7.91; 435/7.92; 436/512; 436/513; 436/514; 436/516

(58) Field of Classification Search .................. 435/7.1, 435/7.2, 7.92; 436/512, 513, 514
See application file for complete search history.

(56) References Cited

U.S. PATENT DOCUMENTS

| 5,190,922 A | 3/1993 | Luly et al. |
| 5,663,148 A | 9/1997 | Or et al. |
| 5,861,272 A | 1/1999 | Li et al. |

OTHER PUBLICATIONS

Teran et al. (Clinical Experimental Allergy 1997 vol. 27, p. 396-405).*

* cited by examiner

*Primary Examiner*—Long V. Le
*Assistant Examiner*—Changhwa J Cheu
(74) *Attorney, Agent, or Firm*—Scully, Scott, Murphy & Presser, P.C.

(57) ABSTRACT

This invention provides the first blood test which characterizes asthma severity. More specifically, the present invention provides methods of determining the severity of acute asthma in a patient by determining the levels of C5a or C5a-desArg in the patient's blood, plasma or serum.

5 Claims, 4 Drawing Sheets

US 7,407,764 B2

PLASMA C5A LEVELS AS AN INDICATOR OF ASTHMA SEVERITY

CROSS REFERENCE TO RELATED APPLICATIONS

This application is a continuation-in-part of International Application No. PCT/US2004/011348 filed Apr. 13, 2004, which claims the benefit of U.S. Provisional Application No. 60/463,646 filed Apr. 17, 2003.

FIELD OF THE INVENTION

This invention relates to methods for determining asthma severity. More specifically, the present invention relates to methods of determining the severity of acute asthma in a patient by determining the C5a level in the patient's plasma blood, serum or plasma.

BACKGROUND OF THE INVENTION

The prevalence and severity of asthma have increased dramatically in recent decades. It is generally accepted that asthma arises as a result of inappropriate immunological responses to common environmental antigens in genetically susceptible individuals (Willis-Karp, M., "Immunologic basis of antigen-induced airway hyperresponsiveness," *Ann. Rev. Immunol.* 17: 255-281 (1999)). Recently, the gene encoding complement factor 5 (C5) has been identified as a susceptibility locus for allergen-induced airway hyperresponsiveness in a murine model of asthma (Karp et al., *Nature Immunology* 1: 221-225, 2000).

Activation of the classical, lectin complement pathways can result in proteolytic cleavage of C5 to two fragments, C5a and C5b, both of which can stimulate cytokine production. As part of a hemolytically active membrane attack complex, C5b causes signaling in neutrophils and endothelia, inducing chemokine production by the latter (Wang et al., *Blood* 85: 2570-2578, 1995; Wang et al., *J. Immunol.* 156: 786-792, 1996; Kilgore et al., *Am J. Pathol.* 150: 2019-2031, 1997). C5a has pleiotropic effects on inflammation, being chemotactic for all myeloid lineages, inducing degranulation and the production of a variety of proinflammatory mediators by granulocytes and increasing vascular permeability (Gerard et al., *Annu. Rev. Immunol.* 164: 3009-3017, 2000). C5a also stimulates monocyte and macrophage production of the proinflammatory cytokines TNF-α, IL-1 and IL-6 (Morgan et al., *J. Immunol.* 148: 3937-3942, 1992; Schindler et al., *Blood* 76: 1631-1638, 1990; Cavaillon et al., *Eur. J. Immunol.* 20: 253-257, 1990). Inhibition of stimulation of monocytes and macrophages by C5a through the C5a receptor has resulted in the inhibition of production of IL-12 (Karp, *Nature Immun.*, 2000), a Th1 promoting cytokine, by these cells.

The nascent C5a fragment of C5, once formed in blood plasma or serum, is rapidly cleaved to the C5a-desArg form by the endogenous serum carboxypeptidase N enzyme (Bokisch et al. *J. Clin. Invest.* 49: 2427-36, 1970).

Prior to the present invention, there is no recognition that the plasma levels of C5a or levels of C5a-desArg in asthma patients correlate with the severity of asthma.

SUMMARY OF THE INVENTION

The present inventors have unexpectedly discovered that the plasma C5a levels in asthma patients correlate with the severity of asthma determined by using conventional clinical criteria. Particularly, the present invention recognizes that there is a significant inverse correlation between plasma C5a levels and asthma severity in pediatric patients while increased asthma severity scores correlated with increased C5a in adult patients.

Accordingly, in one embodiment, the present invention provides a method of determining the severity of asthma in a patient by detecting the level of C5a or C5a-desArg in a blood, plasma or serum sample from the patient.

In another embodiment, the present invention provides a method of determining the severity of asthma in a patient by detecting the level of C5a or C5a-desArg in a blood, plasma or serum sample from the patient, and correlating the level with an asthma severity score.

DETAILED DESCRIPTION OF THE INVENTION

Figure 1:
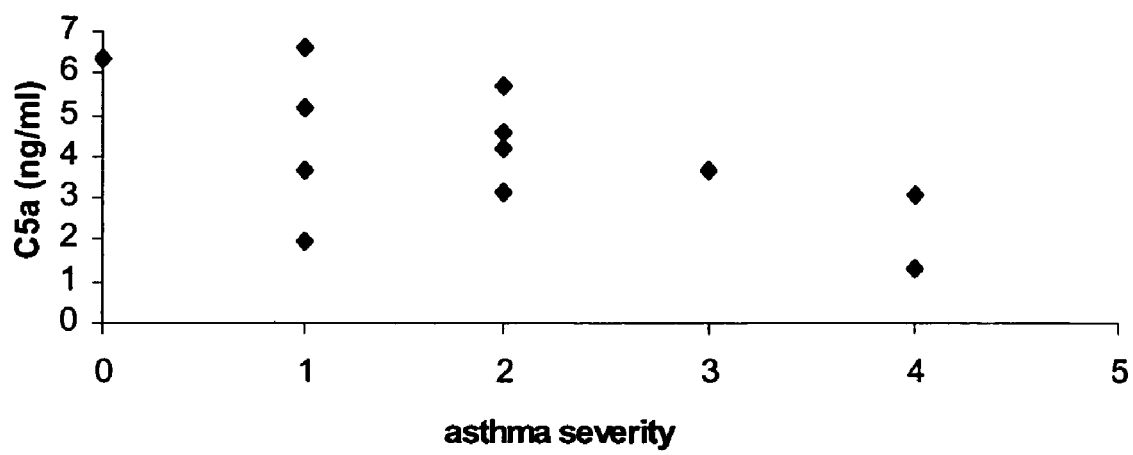
FIG. 1 depicts correlation of pediatric asthma severity (n=12) with plasma C5a levels (R=−0.60, p=0.38).

The present inventors have surprisingly found that the plasma C5a-desArg levels in asthma patients correlate with the severity of asthma determined by using conventional clinical criteria. Particularly, the present invention recognizes that there is a significant inverse correlation between plasma C5a levels and asthma severity in pediatric clinical patients, while increased asthma severity scores correlate with increased C5a in adult clinical patients. Accordingly, the present invention provides for the first time a blood test method for determining the severity of asthma in a patient.

By "children" or "pediatric group" is meant young or not fully developed persons, particularly between infancy and youth. According to the present invention, children can be persons at the ages ranging from newborn to about 18 years old, preferably, about 6 months old to about 18 years old. By "adults" is meant fully developed and mature persons, particularly, persons at an age above 18 years old.

In one embodiment, the present invention provides a method for determining the severity of asthma in a patient by detecting the level of C5a or C5a-desArg in the patient's blood.

To detect the blood level of C5a or C5a-desArg in a patient, a blood sample is taken from the patient. The blood sample can be a sample of whole blood drawn from the patient, or a sample of the serum or plasma portion derived from whole blood of the patient. Methods for obtaining the plasma or serum portion of whole blood are well known in the art and are also illustrated in Example 2, provided hereinbelow.

Detection of the levels of C5a or C5a-desArg in patients' blood can be carried out by using antibodies specific for C5a or C5a-desArg in any enzyme-immunological or immunochemical detection format, such as ELISA (enzyme linked immunosorbent assay), EIA (enzyme immunoassay), RIA (radioimmunoassay), Western Blot analysis, DIPSTICK and the like. Depending upon the assay used, the blood samples or the antibodies can be labeled by an enzyme, a fluorophore or a radioisotope. See, e.g., Coligan et al. *Current Protocols in*

*Immunology*, John Wiley & Sons Inc., New York, N.Y. (1994); and Frye et al., *Oncogen* 4: 1153-1157, 1987. Preferably, the detection is carried out using an ELISA assay where labeled antibodies against C5a-desArg are immobilized, as exemplified in Example 2 hereinbelow.

*of Allergy & Clinical Immunology* 111(2): S507, 2003. This severity scoring system, developed by the National Heart, Lung, and Blood Institute (NHLBI), combines evaluations of symptoms, amounts of β-2 agonist rescue inhaler used to treat symptoms, and lung function (see Table 1).

TABLE 1

| | | Classify Severity: Clinical Features Before Treatment or Adequate Control | | Medications Required to Maintain |
|---|---|---|---|---|
| Score | | Symptoms/Day Symptoms/Night | PEF or FEV$_1$ PEF Variability | Long-Term Control Daily Medications |
| 4 | Step 4 Severe Persistent | Continual Frequent | ≦60% >30% | Preferred treatment: High-dose inhaled corticosteroids AND Long-acting inhaled beta$_2$-agonists AND, if needed, Corticosteroids tablets or syrup long term (2 mg/kg/day, generally do not exceed 60 mg per day). (Make repeat attempts to reduce systemic corticosteroids). |
| 3 | Step 3 Moderate Persistent | Daily >1 night/week | >60%-<80% >30% | Preferred treatment: Low-to medium dose inhaled corticosteroids and long-acting inhaled beta$_2$-agonists. Alternative treatment (listed alphabetically): Increase inhaled corticosteroids within medium-dose range OR Low-to-medium dose inhaled corticosteroids and either leukotriene modifier or theophylline. If needed (particularly in patients with recurring severe exacerbations): Preferred treatment: Increase inhaled corticosteroids within medium-dose range and add long-acting inhaled beta$_2$-agonists. Alternative treatment: Increase inhaled corticosteroids within medium-dose range and add either leukotriene modifier or theophylline. |
| 2 | Step 2 Mild Persistent | >2/week but <1x/day >2 nights/month | >80% 20-30% | Preferred treatment: Low-dose inhaled corticosteroids. Alternative treatment (listed alphabetically): cromolyn, leukotriene modifier, nedocromil, OR sustained release theophylline to serum concentration of 5-15 mcg/mL. |
| 1 | Step 1 Mild Intermittent | ≦2 days/week ≦2 nights/month | ≧80% <20% | No daily medication needed. Severe exacerbations may occur, separated by long periods of normal lung function and no symptoms. A course of systemic corticosteroids is recommended. |

PEF is % of personal best;
FEV$_1$ is % predicted.

In another embodiment, the present invention provides a method of determining the asthma severity of a patient by detecting the level of C5a or C5a-desArg in a blood, plasma or serum sample from the patient, and correlating such level with an asthma severity score.

As discovered by the present inventors, blood levels of C5a or C5a-desArg in asthma patients correlate with asthma severity scores determined using conventional clinical criteria. Particularly, the present invention recognizes that there is a significant inverse correlation between plasma C5a levels and asthma severity in pediatric clinical groups, while increased asthma severity scores correlated with increased C5a in adult clinical groups. Conventional clinical criteria used in determining asthma severity scores are described in *J.*

According to the present invention, once the level of C5a or C5a-desArg in a patient's blood is determined, such level can be compared to a predetermined value of C5a or C5a-desArg levels, or preferably, to a set of predetermined values of C5a or C5a-desArg levels, where each predetermined value corresponds to an asthma severity score determined based on conventional clinical criteria.

Generally speaking, in pediatric patients, a plasma C5a-desArg level above about 6.0 ng/ml, or preferably, above about 6.5 ng/ml, or even more preferably, above about 7.0 ng/ml, correlate with the asthma severity score of "0". A plasma C5a-desArg level of between about 4.0 to about 7.0 ng/ml, or preferably, between about 5.0 to about 6.5 ng/ml, or even more preferably, about 5.5 ng/ml, correlate with the asthma severity score of "1". A plasma C5a-desArg level of between about 3.0 to about 5.0 ng/ml, or preferably, between about 4.0 to about 5.0 ng/ml, or even more preferably, about 4.5 ng/ml, correlate with the asthma severity score of "2". A plasma C5a-desArg level of between about 2.0 to about 4.0 ng/ml, or preferably, between about 2.5 to about 3.5 ng/ml, or even more preferably, about 2.9 ng/ml, correlate with the asthma severity score of "3." A plasma C5a-desArg level below about 3.0 ng/ml, or preferably, below about 2.5 ng/ml, or even more preferably, below about 2.0 ng/ml, correlate with the asthma severity score of "4".

Asthma severity in adults can be measured by any well established methods in the art. For example, asthma severity can be determined by using NIH adult asthma severity score. Generally speaking, in adult patients, a plasma C5a-desArg level of about 2.0 to about 3.0 ng/ml, correlates with an asthma severity of "0." A plasma C5a-desArg level about 3 to about 4 correlates with an asthma severity score of "2." A plasma C5a-desArg level of about 5 and above correlates with an asthma severity score of 4.

Asthma severity in adults can also be measured by self reported asthma symptoms in the adults to be treated or tested. Any well-known self reporting method, e.g., in a form of questionnaire, for measuring asthma severity can be adopted. For example, the Asthma Quality of Life Questionnaire (AQLQ) (Juniper et al., Evaluation of impairment of health related quality of life in asthma: development of a questionnaire for use in clinical trials. *Thorax* 47:76-83, 1992) is preferably employed by the present invention, which is incorporated by reference. The questionnaire (AQLQ) is a validated asthma-specific document. Adult patients rate the degree impairment caused by asthma during the preceding about 14 days and respond to each of 32 items using a 7-point scale on which a score of 1 indicates maximal impairment and 7 indicates no impairment. The questionnaire provides scores in limitation of activities, asthma symptoms, emotional functioning and symptoms from environmental exposure. According to the present invention, the responses are grouped and a total score is generated for each subject. Greater total AQLQ scores are indicative of decreased symptoms of asthma.

Generally speaking, in adult patients, a plasma C5a-desArg level of about 1.0 to about 2.0 ng/ml, correlates with an asthma total AQLQ severity of about 175. A plasma level about 3 to about 4 correlates with an asthma total AQLQ severity score of about 120 to about 160. A plasma C5a-desArg level of about 5 and above correlates with an asthma total AQLQ severity score of about 80 to about 120.

The present invention is further illustrated by the following non-limiting examples.

EXAMPLE 1

Determination of Plasma C5a/C5a-desArg Levels

Plasma was obtained from blood drawn on patients on a single visit. The patients were seen regularly in the Asthma Center Of Excellence at State University of New York at Brooklyn, N.Y. In addition to review of asthma symptoms, the patients were also clinically assessed for presence and degree of allergic rhinitis as well as allergen sensitization (by skin prick testing). At a later time, the patients' asthma severity scores were determined using standardized criteria based on the guidelines provided by the National Lung, Heart and Blood Institute or determined by AQLQ questionnaire.

Plasma C5a/C5a-desArg levels were determined by using the OptEIA™ human C5a kit from PHARMINGEN, a division of Becton, Dickinson and Company, 10975 Torregyana Road, San Diego, Calif. 92121, and following the manufacturer's instructions (provided in Example 2).

Figure 2:
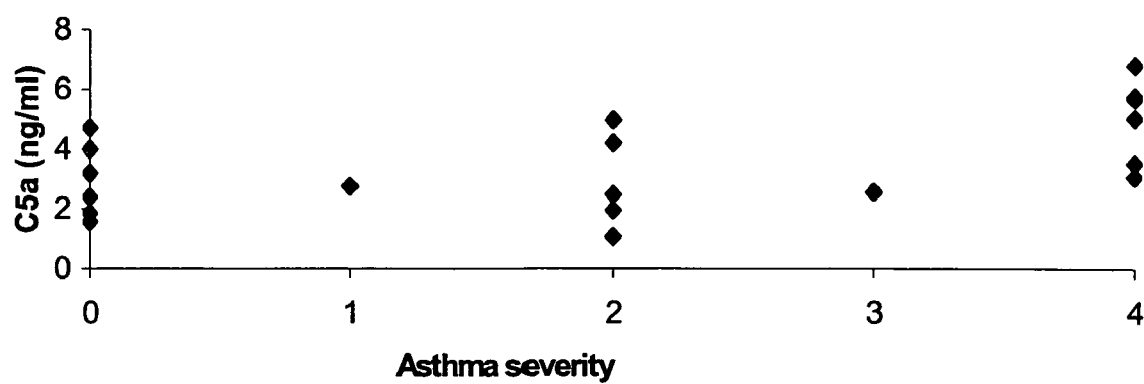
FIG. 2 depicts correlation of asthma severity in adults (n=19) with plasma C5a levels (R=0.52, p=0.02).
Figure 3:
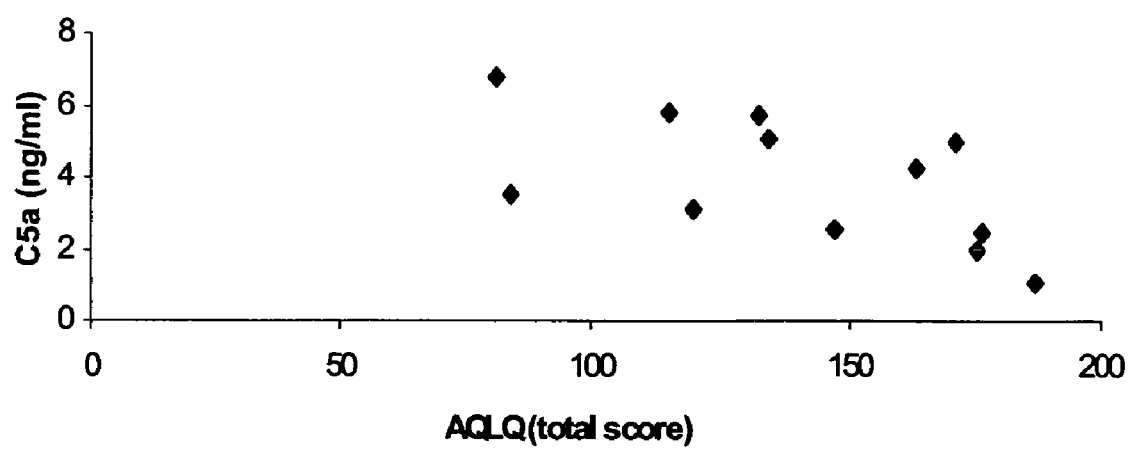
FIG. 3 depicts correlation of asthma symptoms (AQLQ) in adults (n=12) with plasma C5a levels (R=−0.73, p<0.01). Greater scores are indicative of decreased symptoms.

As shown in Tables 2-4 and FIGS. 1-3, the plasma levels of C5a/C5a-desArg in the patients correlate with the asthma severity scores, determined by conventional clinical criteria or AQLQ.

TABLE 2

Correlation of plasma C5a levels (R = −0.60, p = 0.38) with pediatric asthma severity (n = 12)

| Subject | Asthma Severity Score (0-4) | Plasma C5a-desArg (ng/ml) |
|---|---|---|
| 1 | 4 | 1.33 |
| 2 | 4 | 3.08 |
| 3 | 0 | 6.34 |
| 4 | 3 | 3.67 |
| 5 | 2 | 5.68 |
| 6 | 1 | 3.66 |
| 7 | 2 | 4.19 |
| 8 | 1 | 5.19 |
| 9 | 1 | 6.61 |
| 10 | 2 | 4.6 |
| 11 | 2 | 3.17 |
| 12 | 1 | 1.99 |

TABLE 3

Correlation of asthma severity in adults (n = 19) with plasma C5a levels (R = 0.52, p = 0.02)

| Subject | NIH Asthma Severity Score(0-4) | Plasma C5a Level (ng/ml) |
|---|---|---|
| 1 | 4 | 3.522 |
| 2 | 4 | 5.041 |
| 3 | 4 | 6.812 |
| 4 | 2 | 4.976 |
| 5 | 0 | 1.56 |
| 6 | 0 | 3.987 |
| 7 | 0 | 3.187 |
| 8 | 0 | 1.856 |
| 9 | 4 | 3.075 |
| 10 | 2 | 4.205 |
| 11 | 2 | 1.063 |
| 12 | 3 | 2.562 |
| 13 | 2 | 2.473 |
| 14 | 4 | 5.683 |
| 15 | 0 | 2.392 |
| 16 | 0 | 4.71 |
| 17 | 1 | 2.75 |
| 18 | 4 | 5.77 |
| 19 | 2 | 1.944 |

TABLE 4

Correlation of asthma symptoms (AQLQ) in adults (n = 12) with plasma C5a levels (R = −0.73, p < 0.01) (Greater scores are indicative of decreased symptoms.)

| Subject | AQLQ Asthma Severity Score | Plasma C5a Level (ng/ml) |
|---|---|---|
| 1 | 84 | 3.522 |
| 2 | 134 | 5.041 |
| 3 | 81 | 6.812 |
| 4 | 171 | 4.976 |
| 5 | 120 | 3.075 |
| 6 | 163 | 4.205 |
| 7 | 187 | 1.063 |
| 8 | 147 | 2.562 |
| 9 | 176 | 2.473 |

TABLE 4-continued

Correlation of asthma symptoms (AQLQ) in adults (n = 12)
with plasma C5a levels (R = −0.73, p < 0.01)
(Greater scores are indicative of decreased symptoms.)

| Subject | AQLQ Asthma Severity Score | Plasma C5a Level (ng/ml) |
|---|---|---|
| 10 | 132 | 5.683 |
| 11 | 115 | 5.77 |
| 12 | 175 | 1.944 |

EXAMPLE 2

The OptEIA™ Human C5a Test

Principle of the Test

The OptEIA™ ELISA test is a solid phase sandwich ELISA (Enzyme-Linked Immunosorbent Assay). It utilizes monoclonal antibody specific for human C5a-desArg coated on a 96-well plate. Standards and samples are added to the wells, and any C5a-desArg present binds to the immobilized antibody. The wells are washed and a mixture of biotinylated polyclonal anti-human C5a antibody and avidin-horseradish peroxidase is added, producing an antibody-antigen-antibody "sandwich". The wells are again washed and a substrate solution is added, which produces a blue color in direct proportion to the amount of C5a-desArg present in the initial sample. The Stop Solution changes the color from blue to yellow, and the wells are read at 450 nm.

Reagents Used:
Antibody Coated Wells: 1 plate of 96 breakable wells (12 strips×8 wells) coated with anti-human C5a-desArg monoclonal antibody.
Detection Antibody: 15 ml of biotinylated anti-human C5a polyclonal antibody with 0.15% ProClin-150 as preservative.
Standards: 3 vials lyophilized human serum containing a defined amount of C5a-desArg (quantity as noted on vial label).
Enzyme Concentrate (250×): 150 µl of 250× concentrated Avidin-horseradish peroxidase conjugate with 0.01% thimerosal as preservative.
Standard/Sample Diluent: 15 ml of animal serum with 0.09% sodium azide as preservative.
ELISA Diluent: 6 ml of a buffered protein base with 0.09% sodium azide as preservative.
Wash Concentrate (20×): 100 ml of 20× concentrated detergent solution with 0.02% thimerosal as preservative.
TMB One-Step Substrate Reagent: 15 ml of 3,3',5,5' tetramethylbenzidine (TMB) in buffered solution.
Stop Solution: 13 ml of 1M phosphoric acid.
Plate Sealers: 2 sheets with adhesive backing.

Storage

Keep the unopened kits at 2-8° C. Before use, bring all reagents to room temperature (18-25° C.). Immediately after use, return to proper storage conditions. Lyophilized standards are stable until kit expiration date. After reconstitution, use freshly reconstituted standard within 12 hours (stored at 2-8° C.).

Specimen Collection and Handling

Specimens should be clear, non-hemolyzed and non-lipemic. It is recommended that normal human EDTA plasma samples be used undiluted, i.e., neat in this assay. Samples with expected values higher than the top standard, 40 ng/ml, should be diluted with Standard/Sample Diluent prior to running the assay. All specimen handling operations should be carried out at 4° C. for plasma and for serum (immediately after clotting).

Plasma: Collect plasma using disodium EDTA as the anticoagulant. If possible, collect the plasma into a mixture of disodium EDTA and Futhan[5] to stabilize the sample against spontaneous in vitro complement activation. Immediately centrifuge samples at 4° C. for 15 minutes at 1000×g. Assay immediately or store samples on ice for up to 6 hours before assaying. Aliquots of plasma may also be stored at −70° C. for extended periods of time. Avoid repeated freeze-thaw cycles.

Serum: Use a serum separator tube and allow samples to clot for 60±30 minutes. Centrifuge the samples at 4° C. for 10 minutes at 1000×g. Remove serum and assay immediately or store samples on ice for up to 6 hours before assaying. Aliquots of serum may also be stored at −70° C. for extended periods of time. Avoid repeated freeze-thaw cycles.

Other biological samples: Remove any particulate matter by centrifugation and assay immediately or store samples at −70° C. Avoid repeated freeze/thaw cycles.

Reagent Preparation
1. Bring all reagents to room temperature (18-25° C.) before use.
2. STANDARDS:
   a. Reconstitute 1 vial lyophilized Standard with required volume (noted on vial label) of Standard Diluent to prepare a 40 ng/ml stock standard. Allow the standard to equilibrate for at lest 15 minutes before making dilutions. Vortex to mix.
   b. Ad 300 µl Standard Diluent to 6 tubes. Label as 20 ng/ml, 1.25 ng/ml, and 0.625 ng/ml.
   c. Perform serial dilutions by adding 300 µl of each standard to the next tube and vortexing between each transfer (see figure below). The undiluted standard serves as the high standard (40/ng/ml). The Standard Diluent serves as the zero standard (ng/ml).
3. WORKING DETECTOR
   See Assay Procedure, step 4.
4. WASH BUFFER
   If the Wash Concentrate contains visible crystals, warm to room temperature and mix gently until dissolved. Dilute required quantity of 20× Wash Concentrate with deionized or distilled water, mix. (To prepare 2.0 L, add 100 ml Wash Concentrate to 1900 ml water. At least 500 ml solution should be prepared for a full 96-well plate).
5. TMB ONE-STEP SUBSTRATE REAGENT
   No more than 15 minutes prior to use, add required volume of TMB One-Step Substrate Reagent to a clean tube or reservoir. To prevent contamination, pipette out from the tube/reservoir instead of directly from bottle. Avoid prolonged exposure to light or contact with metal, air, or extreme temperature as color may develop.

Assay Procedure
1. Bring all reagents and samples to room temperature (18-25° C.) prior to use. It is recommended that all standards and samples be run in duplicate. A standard curve is required in each assay run.
2. Place required quantity of test strips/wells in well holder. Wells are provided in breakable 8-well strips. Strips may be "broken" into individual wells, replaced in well holder, and assayed. Return any unused wells to sealed pouch for 2-8° C. storage.

3. Pipette 50 µl of ELISA Diluent into each well.
4. Pipette 100 µl of each standard (see Reagent Preparation, step 2) and sample into appropriate wells. Gently shake/tap the plate for 5 seconds to mix. Cover wells with Plate Sealer and incubate for 2 hours at room temperature.
5. Prepare Working Detector. Within 15 minutes prior to use, pipette required volume of Detection antibody into a clean tube or flask. Add in required quantity of Enzyme Concentrate (250×), vortex or mix well. For a full 96-well plate, add 48 µl of Enzyme Concentrate into 12 ml of Detection Antibody.
6. Decant or aspirate contents of wells. Wash wells by filling with at lest 300 µl/well prepared Wash buffer (see Reagent Preparation, step 4) and then decanting/aspirating. Repeat wash 4 times for a total of 5 washes. After the last wash, blot plate on absorbent paper to remove any residual buffer. Complete removal of liquid is required for proper performance.
7. Add 100 µl of prepared Working Detector (see step 5 above) to each well. Gently shake/tap the plate for 5 seconds to mix. Cover wells with plate Sealer and incubate for 1 hour at room temperature.
8. Wash wells as in Step 6, but a total of 7 times. In this final wash step, soak wells in wash buffer for 30 seconds to 1 minute for each wash. Thorough washing at this step is very important.
9. Add 100 µl of TMB One-Step Substrate Reagent to each well. Gently shake/tap the plate for 5 seconds to mix. Incubate plate (without Plate Sealer) for 30 minutes at room temperature in the dark.
10. Add 50 µl of Stop Solution to each well. Gently shake/tap the plate for 5 seconds to mix.
11. Read absorbance at 450 nm within 30 minutes of stopping reaction. If wavelength correction is available, subtract A (570 nm) from A (450 nm).

Calculation of Results

Calculate the mean absorbance for each set of duplicate standards, controls and samples. Subtract the mean zero standard absorbance from each. Plot the standard curve on log-log graph paper, with C5a-desArg concentration on the x-axis and absorbance on the y-axis. Draw the best fit straight line through the standard points.

To determine the C5a-desArg concentration of the unknowns, find the unknowns' mean absorbance value on the y-axis and draw a horizontal line to the standard curve. At the point of intersection, draw a vertical line to the x-axis and read the C5a-desArg concentration. If samples were diluted, multiply the C5a-desArg concentration by the dilution factor. Computer curve-fitting statistical software may also be employed.

EXAMPLE 3

Relation of Plasma C5a Levels to Allergic Disease in Pediatric and Adult Cohorts Rationale. Murine C5 deficiency has been linked to allergen-induced airway hyperreactivity (Karp, 2000). This deficiency has not been studied in humans. The present studies investigated the relationship of plasma levels of C5a-desArg and other complement split products (CSP) to clinical allergic disease in both pediatric and adult populations.

Method. Plasma levels of C5a/C5a-desArg, C4a-desArg and C3a-desArg (ELISA) were measured from allergic children (n=18) (no immunotherapy) and allergic adults (n=19) (most of whom were receiving immunotherapy). Asthma severity scores (0-4) were assigned according to 2002 NHLBI criteria. Additional data for the adult group included: rhinitis and asthma symptoms scores (RQLQ and AQLQ, Juniper), spirometry, exhaled nitric oxide (eNO), CBC, and T cell studies.

Figure 4:
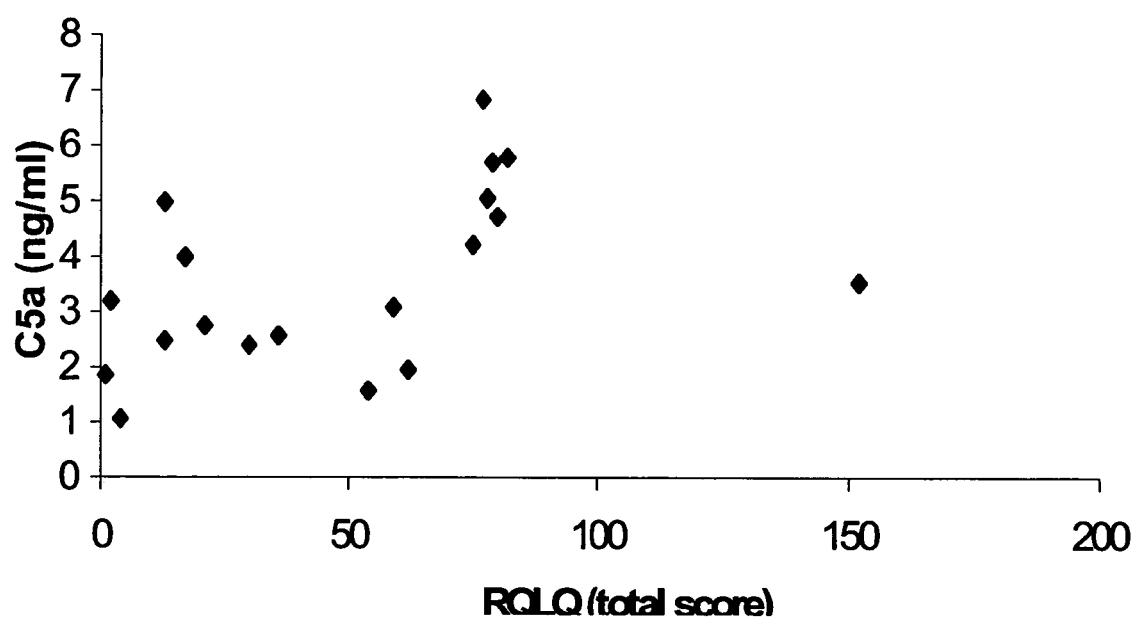
FIG. 4 depicts correlation of rhinoconjunctivitis symptoms (RQLQ) in adults (n=19) with plasma levels of C5a (R=0.59, p<0.01). Greater scores are indicative of increased symptoms.

Results. For the pediatric clinic group, there was a significant inverse correlation between plasma C5a levels and asthma severity ($p=0.038$), but not to IgE ($p=0.46$). No correlation was found between severity and C4a, C3a, or IgE ($p=0.20, 0.66,$ and $0.61$, respectively). Increased adult asthma severity scores correlated with increased C5a ($p=0.02$). In addition, increased rhinoconjunctivitis and asthma symptoms correlated with increased C5a levels ($p=0.008$ and $p=0.0065$, respectively). No other parameter correlated with C5a. C4a levels did not correlate with any clinical or laboratory parameters. See Tables 5-6 and FIG. 4.

Conclusions. Plasma C5a levels correlated with severity of rhinoconjunctivitis. Increased C5a associated with decreased asthma severity in allergic children illustrates that a protective stimulus by C5a are active at young ages. Although not wishing to be bound by any particular theory, it is believed that a protective stimulus by C5a is activated through IL-12 levels. Long term allergen exposure in adults, including by immunotherapy, can increase anaphylatoxin activity and increases allergic responses to C5a.

TABLE 5

Correlation of Plasma C5a-desArg levels with rhinoconjunctivitis clinical severity

| Subject | Rhinoconjunctivitis Severity Score (RQLQ) | Plasma C5a/C5a-desArg (ng/ml) |
| --- | --- | --- |
| MA | 152 | 3.522 |
| SA | 78 | 5.041 |
| PS | 77 | 6.812 |
| DH | 13 | 4.976 |
| MK | 54 | 1.56 |
| AM | 17 | 3.987 |
| DS | 2 | 3.187 |
| rj | 1 | 1.856 |
| csf | 59 | 3.075 |
| aa | 75 | 4.205 |
| wk | 4 | 1.063 |
| IR | 36 | 2.562 |
| IS | 13 | 2.473 |
| vc | 79 | 5.683 |
| dz | 30 | 2.392 |
| cb | 80 | 4.71 |
| mb | 21 | 2.75 |
| yb | 82 | 5.77 |
| dn | 62 | 1.944 |

TABLE 6

Spearman Correlation Coefficients of C5a and C4a with clinical and laboratory parameters

|  | C5a | C4a |
| --- | --- | --- |
| RQLQ | 0.0078 | 0.95 |
| Asthma AQLQ | 0.0065 | 0.17 |
| Asthma severity | 0.0233 | 0.52 |
| IgE | 0.8473 | 0.71 |
| Nitric Oxide (PPB) | 0.3283 | 0.69 |
| FEV1/FEV | 0.5638 | 0.31 |

TABLE 6-continued

Spearman Correlation Coefficients of C5a and C4a
with clinical and laboratory parameters

|  | C5a | C4a |
|---|---|---|
| FEV1 | 0.8277 | 0.54 |
| PEF (peak flow) | 0.1723 | 0.47 |
| PEF 25-75 | 0.4949 | 0.83 |
| PMN | 0.5293 | 0.48 |
| CD4/CD8 | 0.4609 | 0.86 |

We claim:

1. A method of determining the severity of asthma in an adult asthma patient comprising:
   (a) obtaining a blood sample from an adult patient having asthma;
   (b) determining the level of C5a-desArg in the blood of said patient, wherein an elevated level of the C5a-desArg correlates with an increased severity of asthma in said patient.

2. The method of claim 1, wherein said sample is selected from a whole blood sample, a serum sample or a plasma sample.

3. The method of claim 1, wherein the level of C5a-desArg in said sample is detected by an immunological assay.

4. The method of claim 3, wherein said immunological assay is an assay selected from ELISA (enzyme linked immunosorbent assay), EIA (enzyme immunoassay), RIA (radioimmunoassay), or Western Blot analysis.

5. The method of claim 1, further comprising correlating said level to an asthma severity score.

* * * * *